(12) United States Patent
Chevallier

(10) Patent No.: US 11,135,377 B2
(45) Date of Patent: Oct. 5, 2021

(54) NEEDLE SHEATHING DEVICE WITH FLEXIBLE END-PIECE FOR SYRINGE

(71) Applicant: Sanofi, Paris (FR)

(72) Inventor: Stephane Chevallier, Saint Pathus (FR)

(73) Assignee: Sanofi, Paris (FR)

( * ) Notice: Subject to any disclaimer, the term of this patent is extended or adjusted under 35 U.S.C. 154(b) by 129 days.

(21) Appl. No.: 15/419,584

(22) Filed: Jan. 30, 2017

(65) Prior Publication Data

US 2017/0203048 A1 Jul. 20, 2017

Related U.S. Application Data

(63) Continuation of application No. 14/044,081, filed on Oct. 2, 2013, now Pat. No. 9,555,196, which is a (Continued)

(30) Foreign Application Priority Data

Feb. 11, 2002 (FR) ..................... 02/01643

(51) Int. Cl.
*A61M 5/32* (2006.01)
*A61M 5/315* (2006.01)
*A61M 5/31* (2006.01)

(52) U.S. Cl.
CPC ...... *A61M 5/3202* (2013.01); *A61M 5/31511* (2013.01); *A61M 5/3204* (2013.01); (Continued)

(58) Field of Classification Search
CPC .......... A61M 5/326; A61M 2005/3247; A61M 5/3137; A61M 5/3234; A61M 5/3243; (Continued)

(56) References Cited

U.S. PATENT DOCUMENTS

| 2,674,246 A * | 4/1954 | Bower ................... A61M 5/32 604/198 |
| 4,775,369 A | 10/1988 | Schwartz |

(Continued)

FOREIGN PATENT DOCUMENTS

| EP | 0405039 | 1/1991 |
| EP | 0864335 | 9/1998 |

(Continued)

OTHER PUBLICATIONS

French Search Report dated Oct. 23, 2002 for French Application No. 0201643.

(Continued)

*Primary Examiner* — Bradley J Osinski
(74) *Attorney, Agent, or Firm* — Fish & Richardson P.C.

(57) ABSTRACT

The invention relates to a safe support device for a syringe, said support comprising a support sheath for the body of a syringe, and safety means which comprise an inner sheath suitable for sliding relative to said support sheath between a waiting retracted position, in which said inner sheath is substantially retracted inside said support sheath, and an active protection position, in which said inner sheath projects from said support sheath. The inner sheath has a free end portion formed by a flexible end-piece. The invention also relates to an assembly comprising such a safe support device and a syringe having a body, a piston and a needle disposed at one end of said body.

19 Claims, 3 Drawing Sheets

Related U.S. Application Data continuation of application No. 13/647,928, filed on Oct. 9, 2012, now Pat. No. 8,603,043, which is a continuation of application No. 12/902,655, filed on Oct. 12, 2010, now Pat. No. 8,308,696, which is a continuation of application No. 10/503,229, filed as application No. PCT/FR03/00423 on Feb. 11, 2003, now Pat. No. 7,850,661.

(52) U.S. Cl.
CPC ..... *A61M 5/326* (2013.01); *A61M 2005/3143* (2013.01); *A61M 2005/3247* (2013.01); *A61M 2005/3261* (2013.01); *A61M 2005/3264* (2013.01)

(58) Field of Classification Search
CPC ........ A61M 2005/3139; A61M 5/3257; A61M 5/3271; A61M 2005/3264; A61M 2005/3143; A61M 5/3245; A61M 2005/3246; A61M 2005/3258; A61M 2005/3261; A61M 5/42; A61M 5/3202; A61M 5/31511
See application file for complete search history.

(56) References Cited

U.S. PATENT DOCUMENTS

| | | | |
|---|---|---|---|
| 4,898,589 A | 2/1990 | Dolgin et al. | |
| 4,927,416 A | 5/1990 | Tomkiel | |
| 5,156,599 A * | 10/1992 | Ranford | A61M 5/3271 |
| | | | 128/919 |
| 5,163,918 A * | 11/1992 | Righi | A61M 5/326 |
| | | | 604/198 |
| 5,201,720 A | 4/1993 | Borgia et al. | |
| 5,242,416 A | 9/1993 | Hutson | |
| 5,342,320 A | 8/1994 | Cameron | |
| 5,492,536 A | 2/1996 | Mascia | |
| 5,562,624 A | 10/1996 | Righi et al. | |
| 5,562,626 A | 10/1996 | Sanpietro | |
| 5,591,138 A | 1/1997 | Vaillancourt | |
| 5,746,718 A | 5/1998 | Steyn | |
| 6,110,147 A | 8/2000 | Perouse | |
| 6,159,184 A | 12/2000 | Perez et al. | |
| 6,171,283 B1 | 1/2001 | Perez et al. | |
| 6,186,980 B1 * | 2/2001 | Brunel | A61M 5/3202 |
| | | | 604/110 |
| 6,319,233 B1 * | 11/2001 | Jansen | A61M 5/326 |
| | | | 604/187 |
| 6,319,234 B1 | 11/2001 | Restelli et al. | |
| 6,613,022 B1 * | 9/2003 | Doyle | A61M 5/326 |
| | | | 604/192 |
| 6,623,459 B1 | 9/2003 | Doyle | |
| 6,648,858 B2 | 11/2003 | Asbaghi | |
| 6,679,864 B2 | 1/2004 | Gagnieux et al. | |
| 6,776,777 B2 * | 8/2004 | Barrelle | A61M 5/326 |
| | | | 604/110 |
| 6,913,593 B1 | 7/2005 | Alexandre et al. | |
| 7,101,355 B2 | 9/2006 | Doyle | |
| 7,850,661 B2 | 12/2010 | Chevalier et al. | |
| 8,308,696 B2 | 11/2012 | Chevalier et al. | |
| 8,603,043 B2 | 12/2013 | Chevalier et al. | |
| 2002/0193746 A1 | 12/2002 | Chevallier | |
| 2003/0212380 A1 * | 11/2003 | Barrelle | A61M 5/326 |
| | | | 604/506 |
| 2005/0148943 A1 | 7/2005 | Chevalier et al. | |
| 2008/0294120 A1 | 11/2008 | Chevalier et al. | |
| 2011/0046605 A1 | 2/2011 | Chevalier et al. | |
| 2013/0030377 A1 | 1/2013 | Chevalier et al. | |
| 2014/0031762 A1 | 1/2014 | Chevalier et al. | |

FOREIGN PATENT DOCUMENTS

| | | | |
|---|---|---|---|
| EP | 0966983 | | 12/1999 |
| FR | 2654346 | | 5/1991 |
| FR | 2778853 | | 11/1999 |
| FR | 2801795 | | 6/2001 |
| JP | 11319090 | | 11/1999 |
| WO | WO01/41841 | * | 6/2001 |
| WO | WO 2001/41841 | | 6/2001 |
| WO | WO 2001/85239 | | 11/2001 |
| WO | WO 2003/068298 | | 8/2003 |

OTHER PUBLICATIONS

International Search Report in Application No. PCT/FR2003/00423, dated Jun. 30, 2003, 2 pages.

* cited by examiner

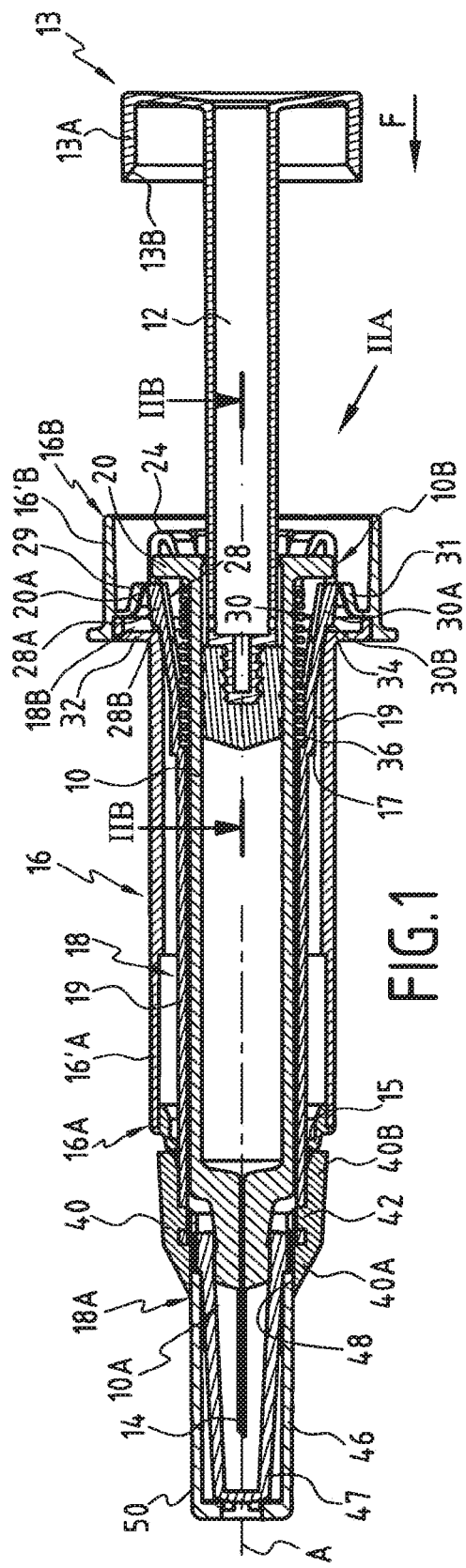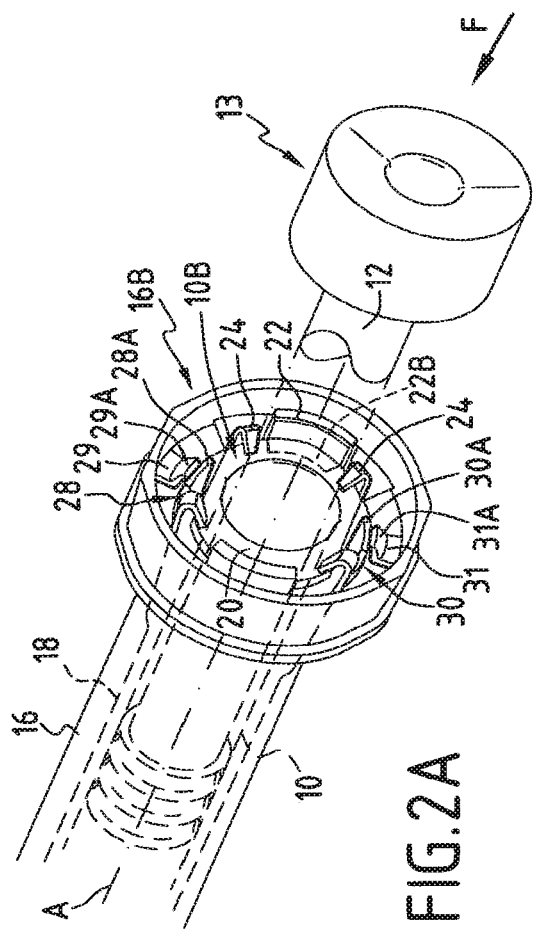

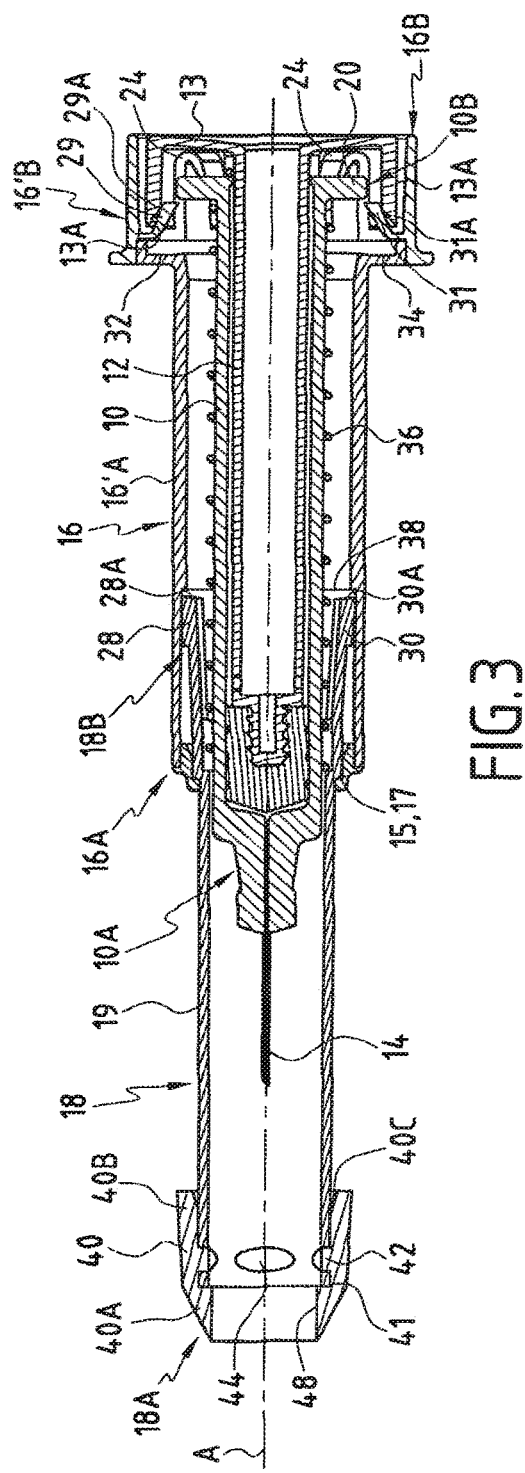
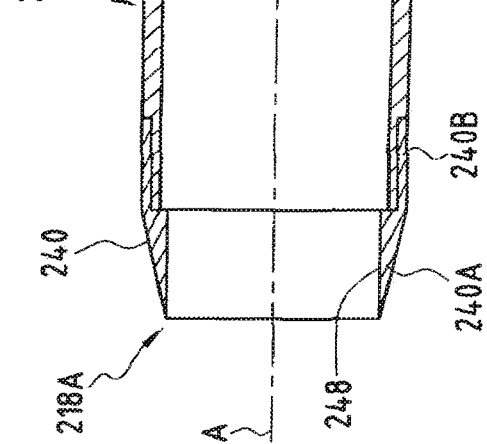
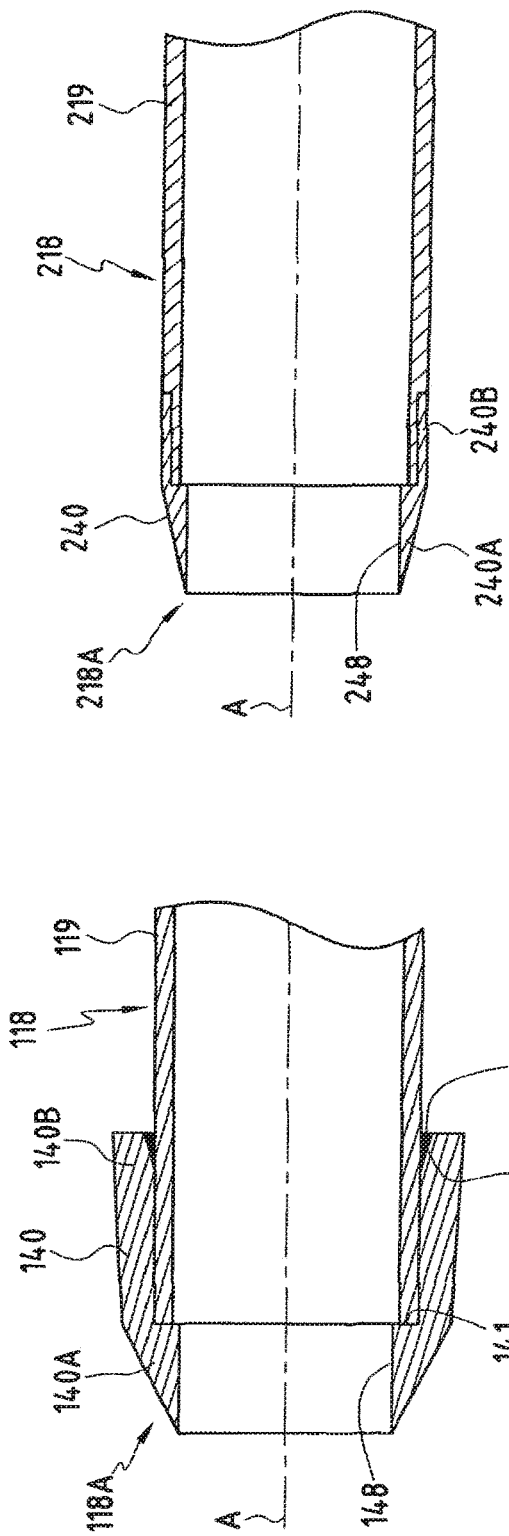
FIG.3
FIG.4
FIG.5

NEEDLE SHEATHING DEVICE WITH FLEXIBLE END-PIECE FOR SYRINGE

CROSS REFERENCE TO RELATED APPLICATIONS

The present application is a continuation of U.S. patent application Ser. No. 14/044,081, filed Oct. 2, 2013, which is a continuation of U.S. patent application Ser. No. 13/647,928, filed Oct. 9, 2012, now U.S. Pat. No. 8,603,043, which is a continuation of U.S. patent application Ser. No. 12/902,655, filed Oct. 12, 2010, now U.S. Pat. No. 8,308,696, which is a continuation of U.S. patent application Ser. No. 10/503,229, filed on Aug. 2, 2004, now U.S. Pat. No. 7,850,661, which is a U.S. National Phase Application pursuant to 35 U.S.C. § 371 of International Application No. PCT/FR03/00423, filed Feb. 11, 2003, which claims priority to French Patent App. No. 02/01643, filed Feb. 11, 2002. The entire disclosure contents of these applications are herewith incorporated by reference into the present application.

BACKGROUND

The present invention relates to a safe support device for a syringe, said safe support device comprising a support sheath for the body of a syringe, and safety means which comprise an inner sheath suitable for sliding relative to said support sheath between a waiting retracted position, in which said inner sheath is substantially retracted inside said support sheath, and an active protection position, in which said inner sheath projects from said support sheath.

The invention also relates to an assembly made up of such a device and of a syringe.

Such a device makes it possible to protect the user against any risk of accidental pricking after the syringe has been used, and therefore against any risk of possible contamination, by surrounding the needle of the syringe with the inner sheath which is driven into its active protection position by drive means such as a spring.

Such devices and assemblies that make it possible to protect the needle by moving an inner sheath inside a support sheath are known.

Document FR 2 801 795 describes an assembly in which the inner sheath can be deployed automatically by drive means (in that example, by resilient means) so as to take up an active protection position around the needle at the end of the injection. However, the first time the inner sheath comes into contact with the skin of the patient can be somewhat unexpected and can surprise the patient, in particular since the contact takes place dynamically. Thereafter, a slight pressure, due to the drive exerted by the resilient means on the inner sheath until it is fully extracted from the support sheath, can be felt by the patient, until the needle is fully withdrawn from the flesh of the patient. However, that pressure is static and therefore there is no risk of causing the patient to suffer bruising.

In that type of device, the resilient means are generally rated to limit the magnitude of the contact pressure, by causing the inner sheath to slide gently out of the support sheath so that it does not slam against the skin of the patient. Thus, the contact against the skin of the patient takes place with gentleness that varies depending on the speed with which the inner sheath is driven out the support sheath, and, in general, depending on the magnitude of the drive exerted by the resilient means on the inner sheath.

However, the impact of the inner sheath against the skin can be unpleasant for the patient who is generally already worried by the injection.

SUMMARY

An object of the invention is to propose a safe support device for a syringe, in which device, at the end of the injection, the inner sheath comes out of the support sheath with the contact pressure between the inner sheath and the skin of the patient being limited.

This object is achieved by means of the fact that the inner sheath has a free end portion formed by a flexible end-piece.

Unlike known devices which require the patient to take up, in the injection zone, some or even all of the energy released by the inner sheath coming into contact with the skin of the patient, because the end of the sheath is rigid, the device of the present invention has a free end portion of the inner sheath that is capable of absorbing at least some of said energy released during the contact, and of damping the contact pressure so that the contact takes place without slamming.

Advantageously, the inner sheath has a rigid first portion via which said inner sheath co-operates with said support sheath, and a second portion formed by said flexible end-piece which is secured to said first portion.

The first portion of the inner sheath is advantageously rigid to avoid any risk of it deflecting while it is sliding inside the support sheath, since such deflecting might impede it as it is coming out.

The end-piece is advantageously fixed to said first portion by means chosen from bonding with an adhesive, overmolding, heat-sealing, or force fitting.

The end-piece and the first portion may then be made in two pieces, and of materials adapted to achieving the desired rigidity.

The end-piece may also be fixed to the first portion of the inner sheath by fixing members. In which case the end-piece is advantageously fixed to said first portion by means made up of first fixing means comprising a projecting member that is part of one of the two elements constituted by said first portion and by said end-piece, and of second fixing means comprising a set-back member that is part of the other of the two elements.

Advantageously the end-piece has a tapering free end, and the material of said end-piece has Shore hardness (Hs) lying in the range 30 Hs to 80 Hs.

Thus, the end-piece is adapted to damp a significant portion of the energy that it has accumulated up until the moment when the inner sheath is deployed at the end of injection. The material of the end-piece and its geometrical shape are preferably selected as a function of the selected drive means. In particular, when said drive means comprise resilient means of known stiffness, the material for the end-piece is selected as a function of the Shore hardness appropriate for damping the contact pressure against the skin of the patient and so that the end-piece can take up a sufficient portion of the energy accumulated in the resilient means.

The device further advantageously comprises retaining means suitable for taking up a retaining active position in which they retain said inner sheath in the waiting retracted position, and an inactive position in which they allow said inner sheath to be deployed under the action of drive means.

Advantageously the retaining means comprise resilient retaining tongues and retaining surfaces, said retaining tongues or said retaining surfaces being integral with said inner sheath, said retaining tongues being retained on the retaining surfaces in the active retaining configuration and being suitable for being moved resiliently towards their inactive configuration, in which said retaining tongues are released from said retaining surfaces.

The invention also provides an assembly comprising a device as described above and a syringe having a body, a piston and a needle disposed at one end of said body.

Advantageously, the syringe body is held securely inside said support sheath and said piston of the syringe has a control portion suitable for causing said retaining means to move into their inactive configuration.

The inner sheath and the support sheath form two concentric tubes in which the body of a syringe can be engaged by being wedged relative to the outer tube formed by the support sheath. The user handles the resulting assembly by taking hold of the support, e.g. by wedging it between the index and the middle finger, and by pushing the piston of the syringe to perform the injection, e.g. with the thumb. When the piston reaches the end of its stroke, the retaining means for retaining the inner sheath are deactivated so as to allow the inner sheath to be deployed automatically out of the support sheath, while the syringe body is held securely in said support sheath.

The inner sheath comes into contact with the skin of the patient, and then it slides further out of the support sheath as the needle is being withdrawn gradually from the flesh of the patient, so that there is no risk of the user being injured by being pricked with the needle, since said needle is no longer accessible after the injection. The user therefore does not need to take any special precautions such as changing the positioning of the fingers, which can remain in the same position from the beginning of the injection until the needle has been fully removed from the flesh of the patient.

The retaining tongues are advantageously situated in the vicinity of one end of said support sheath, which end is remote from the needle, and the piston has a drive portion, e.g. its head, suitable for driving said retaining tongues into their inactive configuration.

Thus, at the end of the injection, the user does not need to make any additional movement to enable the inner sheath to be deployed, which takes place before the needle is withdrawn from the flesh of the patient.

Advantageously, the assembly further comprises a removable cap covering the needle so that, when the inner sheath is in the retracted position, the end-piece of the inner sheath surrounds said cap substantially snugly. Said end-piece may even have a small amount of radial elasticity enabling it to fit snugly around the outline of the cap.

The assembly, in particular made up of the syringe body and of the needle, is thus protected from any risk of external contamination, e.g. bacterial contamination, from the time at which it is assembled to the time at which the cap is removed, in particular for performing the injection.

The invention will be better understood and its advantages will appear more clearly on reading the following detailed description of embodiments given by way of non-limiting example.

BRIEF DESCRIPTION OF THE FIGURES

The description refers to the accompanying drawings, in which:

FIG. 1 is a section view of an assembly comprising a safe support device and a syringe, the assembly being shown in the waiting retracted position;

FIG. 2A is a fragmentary perspective view looking along the direction IIA indicated in FIG. 1;

FIG. 3 is a section view of the assembly of FIG. 1 in the active protection position;

FIG. 4 is a fragmentary section view of the front portion of the inner sheath in another embodiment; and FIG. 5 is a fragmentary section view of the front portion of the inner sheath in another embodiment.

DETAILED DESCRIPTION

Figure 2B:
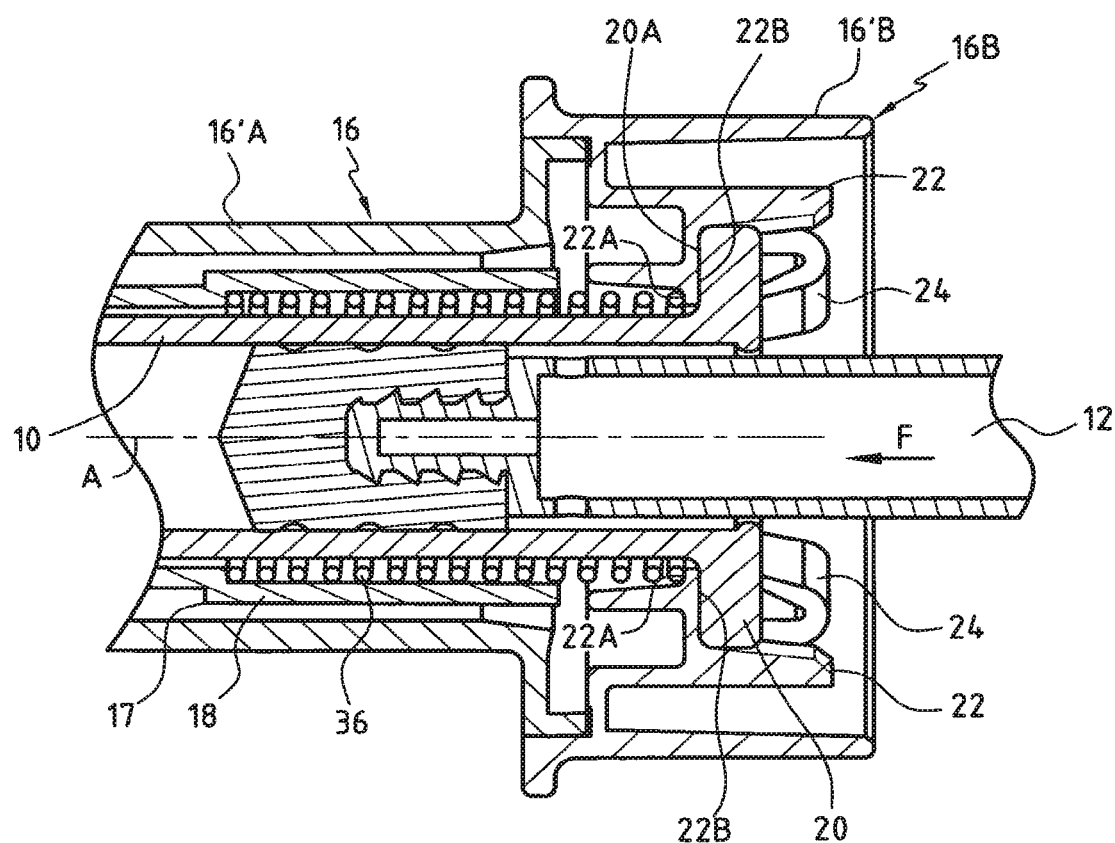
FIG. 2B is a fragmentary section view looking along arrows IIB-IIB of FIG. 1.

The syringe shown in FIGS. 1 to 4 has a body 10 in which a piston 12 is mounted to slide between a waiting for-injection position shown in FIG. 1 and an end-of injection position shown in FIGS. 3 and 4. At that end of the body which is remote from the piston, an injection needle 14 is connected to the body 10. The body of the syringe 10 is preferably made of glass or of plastic.

The safe support device for this syringe comprises a support outer sheath 16 and an inner sheath 18 that is mounted to slide between a waiting retracted position prior to injection, shown in FIG. 1, and an active protection position after injection, shown in FIGS. 3 and 4. In the waiting retracted position prior to injection, the inner sheath 18 is retracted into the outer sheath 16, i.e. it lies almost completely inside said outer sheath, while being disposed around the body 10 of the syringe and while being retained relative to the outer sheath 16 so that the needle 14 projects beyond the respective front ends 16A and 18A of the inner sheath 18 and of the support sheath 16.

Naturally, said front ends 16A and 18A are the ends that are closer to the point of injection, the forward direction being the direction F in which the piston 12 is pushed into the syringe body 10 during injection.

The syringe body 10 is wedged securely relative to the support sheath 16 by wedging means that are part of said sheath 16 and that co-operate with a radial collar 20 provided on the rear end 10B of the syringe body 10 (said rear end being the end remote from the needle 14). The collar 20 is then wedged between an abutment comprising, in this example, two rigid shoulders 22B, each of which is formed from an axial wall portion 22, and snap-fastening catches 24 provided inside said support sheath 16 (e.g. four catches uniformly distributed around the inside periphery of said support sheath). The two axial wall portions 22 are diametrically opposite each other on the support sheath 16.

While the syringe body 10 is being put in place in the safe support device, the snap-fastening catches 24, formed behind the shoulders 22B, move apart resiliently to allow the collar 20 of the syringe body 10 to pass through. Disposed in this way, the collar 20 is securely wedged between the shoulders 22B (in the direction F in which the piston is pushed in) and the snap-fastening catches 24 (in the opposite direction), so that the syringe body 10 is held securely in the support sheath 16 throughout injection, and even while the inner sheath 18 is being deployed automatically into the active protection position.

As can be seen in more detail in FIG. 2A, the rear end portion 18B of the inner sheath 18 is further provided with at least two retaining tongues, for example, axial retaining tongues 28 and 30 having free end portions 28A and 30A, each of which is provided with a respective shoulder 28B, 30B which is hooked onto a respective one of retaining surfaces 32 and 34 that are part of the support sheath 16. In this example, the retaining surfaces 32 and 34 are formed by two respective shoulders or by portions of a circular shoulder. In the active retaining configuration, the retaining tongues 28 and 30, which are resilient, naturally tend to open by moving resiliently apart towards the periphery of the safe support device.

In the active retaining configuration, the retaining tongues 28 and 30 of the inner sheath 18 retain said inner sheath in the waiting retracted position inside the support sheath 16. Naturally, it is possible to imagine forming the tongues on the inside periphery of the outer sheath 16 so that they then hook onto the inner sheath 18, or else that the resilient tongues have a hooking direction that is opposite from the hooking direction shown in FIG. 1 so as to hook onto the collar 20 of the syringe body 10. Regardless of the variant imagined, if, as is advantageously the case, provision is made for the piston 12 to trigger the inner sheath 18, said retaining tongues 28 and 30 must be unhooked when the piston 12 of the syringe reaches an end-of-stroke position.

The respective free ends 28A and 30A of the at least two retaining tongues, for example, the retaining tongues 28 and 30 of the inner sheath 18 come to face at least two activation tongues, for example, resilient activation tongues 29 and 31 which are formed axially on the support sheath 16 and which are suitable for being urged towards an inactive position in which they allow the inner sheath 18 to be deployed out of the support sheath 16. In this example, the activation tongues 29 and 31 can be urged by a control portion of the piston 12.

In the example shown, the head 13 of the piston 12 is provided with said control portion in the form of a forwardly-facing axial flange 13A whose inside periphery slopes so that, when the piston 12 reaches the end of its stroke, said inside periphery 13B co-operates with a first bearing surface and a second bearing surface, for example, bearing surfaces 29AA and 31AA, respectively on ramps 29BB and 31BB on the ends 29A and 31A, respectively, of the activation tongues 29 and 31, and urges them closer together and towards the axis A. By moving towards the axis A, the activation tongues 29 and 31 simultaneously urge the end portions 28A and 30A so that the retaining tongues 28 and 30 themselves move closer together and towards the axis A, thereby releasing their shoulders 28B and 30B from the respective retaining surfaces 32 and 34.

Each of the activation tongues 29 and 31 is disposed between two of the four snap-fastening catches 24, while each of the axial portions 22 is disposed between the other two snap-fastening catches 24, so that alternation of the activation tongue/catch/axial portion/catch type exists over the entire periphery of the support sheath 16.

In order to simplify making the support sheath 16, said support sheath is made up of two portions 16'A and 16'B as in the example shown, the portion 16'A being of relatively simple shape, while the portion 16'B behind the support sheath 16 is of more complex shape and includes the entire set of the tongues 29, 31, of the axial portions 22, and of the catches 24. The two portions 16'A and 161B are held relative to each other by interfitting or by any other known co-operation means.

Drive the piston 12 reaches the end of its stroke, the inner sheath 18 is separated from the support sheath 16 by means of its axial retaining tongues 28 and 30 being released from the respective retaining surfaces 32 and 34.

Drive means, constituted by a spring 36 in this example, help to push the inner sheath 18 forwards (in the direction F indicated in FIG. 1) when the retaining tongues 28 and 30 are released by being pressed by the activation tongues 29 and 31 urged by the head 13 of the piston 12. The spring 36 is received in an annular space provided between the syringe body 10 and the inner sheath 18.

As can be seen in FIG. 2B, the inner sheath 18 has a shoulder 17 formed on its inside periphery and set back relative to the retaining tongues 28 and 30. The shoulder 17 forms an abutment surface for the spring 36.

The rear end of the spring 36 bears against a radial front end face 22A of each of the axial wall portions 22.

Each of the two axial wall portions 22 carries a radial sector projecting towards the axis A of the sheaths 16 and 18, the front faces of said sectors form the front end faces 22A, while their rear faces form the shoulders 22B.

The inner sheath 18 further has a tubular portion 19 formed between the shoulder 17 and the retaining tongues 28 and 30 which extend towards the rear of the inner sheath 18. Said tubular portion has a diameter that is larger than the diameter of the inner sheath 18 and makes it possible to prevent contact between the spring 36 and the retaining tongues 28 and 30, and therefore to prevent any risk of said retaining tongues being damaged, e.g. by rubbing.

The annular space provided for the spring 36 is thus limited by the abutment surface formed by the front end faces 22A, by the shoulder 17, by the tubular portion 19, and by the retaining tongues 28 and 30 In the waiting retracted position, the spring 36 is thus held pre-stressed between the abutment surfaces formed firstly by the front end faces 22A and secondly by the shoulder 17.

After the syringe has been used, in particular at the end of injection, as shown in FIGS. 3 and 4, the piston 12 is at the end of its stroke, and its head 13 comes almost into abutment against the collar 20. The retaining tongues 28 and 30 have been urged by the head, via the activation tongues 29 and 31, so that the retaining tongues 28 and 30 are unhooked from the support sheath 16, and, in this example, from the retaining surfaces 32 and 34.

Since the inner sheath 18 is no longer retained by the retaining tongues 28 and 30 in the support sheath 16, the spring 26 has pushed the inner sheath 18 forwards so that said inner sheath projects to a large extent beyond the front end 16A of the support sheath 16, over a length such that it forms a protection around the needle 14 over a length sufficient to avoid the risks of a user coming into contact with the needle 14.

In this active protection position, the inner sheath 18 is wedged in the forward direction by its shoulder 17 coming into abutment with a shoulder 15 formed internally in a front region of the outer sheath 16. Locking means make it possible to prevent mere pressing on the free end 18A of the inner sheath 18 from enabling said inner sheath 18 to be pushed back into the outer sheath 16, in which case the needle 14 could become accessible to the user.

In this example, said locking means comprise a shoulder 38 formed in the support sheath 16 and facing towards the shoulder 15. The respective free ends 28A and 30A of the axial retaining tongues 28 and 30 are suitable for co-operating with said shoulder 38 so that the inner sheath 18 is wedged between the first shoulder 15 which prevents it from moving forwards in the direction F and the second shoulder 38 which prevents it from returning towards the rear of the safe support device in the direction opposite from the direction in which the inner sheath 18 is deployed.

Since the spring 36 is wedged between the front end face 20A and the shoulder 17, the safe support device can be delivered pre-loaded, with or without the syringe. The syringe is then merely put in place in the safe support device merely by its collar 20 being snap-fastened and by said collar being wedged between the shoulders 22B and the snap-fastening catches 24 on the support sheath 16.

When a syringe is put in place in the safe support device, the user handles the assembly made up of the device and of the syringe by holding the support sheath 16, e.g. between the index and the middle finger, e.g. by wedging those fingers against a collar 16B formed at the rear end of the support sheath 16, and by operating the piston 12 with the thumb, for example.

The inner sheath 18 is deployed automatically, without any additional action being required from the user, as soon as the piston 12 reaches the end of its stroke. Appropriately choosing the stiffness of the spring 36 makes it possible to regulate the deployment of the inner sheath 18 from the support sheath and to limit the extent to which it presses against the skin of the patient.

In addition, in order to damp the contact pressure due to the inner sheath 18 hitting the skin of the patient, the inner sheath 18 is provided with a flexible end-piece on its front portion. The free end of said end-piece 40 forms the free end 18A of the inner sheath 18.

In the example shown, the inner sheath 18 is made up of two portions of different rigidities: namely a rigid first portion 19 via which the inner sheath 18 cooperates with the support sheath 16, and a second portion formed by the flexible end-piece 40 of the first portion 19.

Conventionally, the support sheath 16 and the inner sheath 18 are tubular and made of plastic. In the example shown, the entire first portion 19 is rigid, but the inner sheath 18 could have portions of various flexibilities having rigid zones that enable it to slide without deforming in the support sheath 16, and thus to avoid any risk of the inner sheath jamming by deflecting in said support sheath. For example, the rigid zones could be formed by longitudinal rectilinear tabs that extend along the first portion 19 of the inner sheath 18.

Since the second portion of the inner sheath, which portion is formed by the end-piece 40, serves to damp the contact pressure when the inner sheath 18 is deployed, it is preferably formed by a plastics material chosen from polyvinyl chlorides (PVCs), polyethylenes, elastomers, or rubber. The material forming the end-piece 40 advantageously has Shore hardness lying in the range 30 Hs to 80 Hs, and preferably lying in the range 40 Hs to 50 Hs, in order to guarantee good damping, even in the event that the inner sheath 18 is deployed violently, e.g. due to failure of the retaining means.

In addition, in the example shown, the end-piece 40 has a thickness that tapers towards the front. In this example, the end-piece 40 has a first portion 40B that is substantially tubular, and a front portion 40A that is substantially frustoconical and whose end tapers towards the front of the safety device.

With the end-piece 40 having such a shape, when the inner sheath 18 is deployed from the support sheath 16 and when said inner sheath 18 comes into contact against the skin of the patient, at least a portion of the energy accumulated by the spring 36, which portion has not been released by the inner sheath 18 moving inside the support sheath 16, is taken up by the end-piece 40 deforming.

In a first embodiment, shown in FIG. 3, said end-piece 40 is formed by an additional part which is fixed to the first portion of the inner sheath 18 by fixing means made up of first fixing means comprising at least one projecting member and of second fixing means comprising at least one set-back member.

In the example shown in FIG. 3, the projecting member is constituted by a bead 42 formed on the inside periphery of the end-piece 40, and the set-back member is formed by a notch 44 provided in the first portion 19 of the inner sheath 18. In order to facilitate putting the end-piece 40 in place, said end-piece has a slightly flared opening 400 at its rear end so as to facilitate inserting the inner sheath 18. In addition, in order to guarantee that the inner sheath 18 is positioned properly in the end-piece 40 at the time at which the beads 42 are snap-fastened into the notches 44, the end-piece 40 has an internal shoulder 41 against which the free end of the inner sheath 18 comes into abutment.

It is also possible to imagine making provision for the beads 42 to be formed on the first portion 19 of the inner sheath 18, and for the end-piece 40 to be provided with notches 44 designed to co-operate with beads 42, or for said first portion 19 and the end-piece 40 each to be provided with a bead and with a notch, the bead on one co-operating with the notch in the other. In this embodiment, all of the possible shapes for the projecting member and for the set-back member that make it possible for the end-piece 40 to co-operate with the first portion 19 of the inner sheath 18 can be imagined.

In another embodiment, the end-piece 140 is fixed to the first portion 119 of the inner sheath 118, merely by the end-piece 140 being fitted by force onto the free end of the first portion 119, as shown in FIG. 4. The pressure exerted between the end-piece 140 and the first portion 119 then suffices to hold the end-piece 140 on said first portion.

The end-piece 140 can also be fixed to the first portion 119 of the inner sheath 118 by means 45 chosen from bonding with adhesive, overmolding, or heat-sealing in order to hold it in position.

In this embodiment, the end-piece is externally the same as the above-described end-piece 40, with an identical frustoconical portion 140A. Since beads are omitted, the inside of the portion 140B is simplified and has a cylindrical shape of inside diameter corresponding to the outside diameter of the first portion 119 of the inner sheath 118, and the cylindrical inside portion extends to the shoulder 141. Filling the flared opening 1400 (opposite from the front 118A) with an adhesive 45 makes it possible for the end piece 140 to be held securely onto the first portion 119 of the inner sheath 118.

In another embodiment shown in FIG. 5, the end-piece 240 can be formed directly by molding at the of the first portion 219 of the inner sheath 118, which then forms a single integral piece. In which case, two materials, of different rigidities, are injected into a mold at the corresponding zones, so as to obtain an inner sheath 218 having a rigid portion 219 and a flexible portion 240. The end-piece 240 then preferably has a rear portion 2408 whose shape makes it possible for good bonding to be achieved between the materials forming the end-piece 240 and the first portion 219. The front portion 218 tapers, as in the other embodiments, with an inside outline 248 suitable for co-operating with a cap (not shown).

Regardless of the variant envisaged, the end-piece must be sufficiently flexible to damp the contact pressures when the inner sheath hits the skin of the patient, but it is preferable, for hygiene reasons, to prevent the end-piece from being able to come into contact with a portion of the needle. The end-piece deforming must not enable it to touch the needle, even when considerable pressure, e.g. due to the end-piece being flattened, is exerted on said end-piece. For example, depending on the hardness of the material, the free end of the end-piece can be positioned flush with that end of the syringe body which is close to the needle, in the waiting retracted position.

The assembly formed by the safe support device and by the syringe is further provided with a removable cap that protects the needle prior to use, and in particular when the inner sheath 18 is in the waiting retracted position. The cap protects the needle 14 of the syringe, and co-operates with the syringe body 18 over the front portion 10A thereof. In this example, the cap 46 shown in FIG. 1 is in two portions 46 and 47, disposed one around the other.

When the inner sheath 18 is in the waiting retracted position, the end-piece 40 surrounds the cap 46 substantially snugly, so as to protect the syringe and the needle 14 from all external contamination by substantially leaktight coupling. In this example, the end-piece 40 has an inside outline 48 of geometrical shape substantially identical to the geometrical shape of the outside outline of the cap 46. The cap 46 is frequently of frustoconical shape flaring towards its opening, so that it suffices to choose an inside outline 48 for the end-piece 40 of diameter substantially equal to the mean diameter of the outside outline 40 of the cap 46. Thus, the end-piece 40 co-operates with the cap 46 by the end-piece 40 deforming slightly to fit snugly over the outline of the cap 46. The removable cap 46 is taken off by the user prior to injection, merely by pulling the cap 46 using one hand, for example, while the other hand of the user retains the safe support device.

The invention claimed is:

1. A safety syringe assembly support system for use with a syringe, the syringe comprising a distal end from which a needle distally extends and a proximal end opposite the distal end, the support system comprising:
 a first sheath having a proximal end and a distal end, the first sheath comprising
  a sheath body;
  a shoulder located proximal to the sheath body;
  a tubular portion located proximal to the shoulder; and
  at least two retaining tongues extending proximally from the tubular portion toward the proximal end of the first sheath; and
 a second sheath comprising a radial collar, the second sheath configured to receive the syringe, and the first sheath being disposed in the second sheath such that the distal end of the syringe is closer to the distal end of the first sheath than to the proximal end of the first sheath when the first sheath is in a start position and the syringe is disposed in the second sheath; and
 a pre-stressed spring configured to exert a biasing force on the shoulder of the first sheath and the radial collar of the second sheath when the first sheath is in the start position,
 wherein the first sheath is configured to be moved distally by the biasing force of the spring relative to the second sheath from the start position to a final position, and
 wherein a diameter of the tubular portion of the first sheath is larger than a diameter of the sheath body of the first sheath, wherein the larger diameter of the tubular portion allows the spring to avoid contacting the at least two retaining tongues when the first sheath and the second sheath move relative to each other from the start position to the final position.

2. The safety syringe assembly support system of claim 1, wherein the first sheath comprises at least one flexible portion.

3. The safety syringe assembly support system of claim 2, wherein the at least one flexible portion is located at the distal end of the first sheath.

4. The safety syringe assembly support system of claim 2, wherein the at least one flexible portion is an end-piece located at the distal end of the first sheath.

5. The safety syringe assembly support system of claim 4, wherein the end-piece has a tapering frustoconical free end.

6. The safety syringe assembly support system of claim 4, wherein the end-piece has a flared free end.

7. The safety syringe assembly support system of claim 4, wherein the end-piece comprises an internal shoulder configured to abut the sheath body of the first sheath.

8. The safety syringe assembly support system of claim 4, wherein the end-piece comprises a bead configured to snap into a corresponding notch on the sheath body of the first sheath.

9. The safety syringe assembly support system of claim 4, wherein an inside diameter of the end-piece corresponds with an outside diameter of the sheath body of the first sheath.

10. The safety syringe support system of claim 9, wherein the end-piece is bonded to the sheath body of the first sheath with one of adhesive, overmolding, and heat-sealing.

11. The safety syringe assembly support system of claim 2, wherein the first sheath has rigid zones formed by longitudinal rectilinear tabs extending along the sheath body of the first sheath.

12. The safety syringe assembly support system of claim 1, wherein the at least two retaining tongues of the first sheath engage with retaining surfaces on the second sheath when the first sheath is in the start position.

13. The safety syringe assembly support system of claim 12, further comprising at least two activation tongues on the second sheath configured to cooperate with a periphery of a syringe head of the syringe such that when the syringe head engages the at least two activation tongues, the at least two activation tongues of the second sheath are radially deflected urging the at least two retaining tongues to disengage from the retaining surfaces on the second sheath causing the first sheath to move relative to the second sheath from the start position to the final position.

14. The safety syringe assembly support system of claim 1, wherein a distal end of the second sheath comprises a shoulder configured to abut the shoulder of the first sheath when the first sheath is in the final position.

15. The safety syringe assembly support system of claim 1, wherein when the first sheath is in the start position and the syringe is mounted in the second sheath, the needle projects beyond a distal end of the second sheath, and wherein when the first sheath is in the final position and the syringe is mounted in the second sheath, the first sheath forms a protective shield around the needle.

16. An assembly, comprising:
 a syringe, comprising:
  a syringe body having a distal end and a proximal end opposite the distal end;
  a piston having a free proximal end and a distal end, the free proximal end of the piston having a head and the distal end received within the syringe body; and
  a needle extending distally from the distal end of the syringe body;
 a removable cap covering the needle; and
 a safe support device for the syringe, the safe support device comprising:
  a first sheath having a proximal end and a distal end, the first sheath comprising:

a sheath body;

a shoulder located proximal to the sheath body;

a tubular portion located proximal to the shoulder; and at least two retaining tongues extending proximally from the tubular portion toward the proximal end of the first sheath;

a second sheath comprising a radial collar, the second sheath configured to receive the syringe, the first sheath being disposed in the second sheath, wherein the distal end of the syringe is closer to the distal end of the first sheath than to the proximal end of the first sheath when the first sheath is in a start position and the syringe is disposed in the second sheath; and a pre-stressed spring configured to exert a biasing force on the shoulder of the first sheath and the radial collar of the second sheath when the first sheath is in the start position, wherein the first sheath is configured to be moved distally by the biasing force of the spring relative to the second sheath from the start position to a final position, and wherein a diameter of the tubular portion of the first sheath is larger than a diameter of the sheath body of the first sheath, wherein the larger diameter of the tubular portion allows the spring to avoid contacting the at least two retaining tongues when the first sheath and the second sheath move relative to each other from the start position to the final position.

17. The assembly of claim 16, wherein the first sheath comprises at least one flexible portion.

18. The assembly of claim 17, wherein the at least one flexible portion is an end-piece located at the distal end of the first sheath.

19. The assembly of claim 17, wherein the first sheath comprises rigid zones formed by longitudinal rectilinear tabs extending along the sheath body of the first sheath.

* * * * *

UNITED STATES PATENT AND TRADEMARK OFFICE
CERTIFICATE OF CORRECTION

| | | |
|---|---|---|
| PATENT NO. | : 11,135,377 B2 | |
| APPLICATION NO. | : 15/419584 | |
| DATED | : October 5, 2021 | |
| INVENTOR(S) | : Stephane Chevallier | |

It is certified that error appears in the above-identified patent and that said Letters Patent is hereby corrected as shown below:

In the Claims

In Column 10, Line 22, in Claim 10, after "syringe" insert -- assembly --

Signed and Sealed this
Twenty-eighth Day of June, 2022

Katherine Kelly Vidal
*Director of the United States Patent and Trademark Office*